(12) United States Patent
Sherry et al.

(10) Patent No.: US 8,052,689 B2
(45) Date of Patent: Nov. 8, 2011

(54) CUT-OFF ACETABULAR REAMER

(75) Inventors: Eugene Sherry, Alexandria (AU);
Sureshan Sivananthan, London (GB);
Patrick Hans Heinrich Warnke,
Augustfehn (DE); Andreas Baenziger,
Heiden (CH); Patrick White, West
Chester, PA (US); Patrick Berdoz,
Chester Springs, PA (US); **Fabrice
Chenaux**, Exton, PA (US)

(73) Assignee: Greatbatch Medical S.A., Orvin (CH)

( * ) Notice: Subject to any disclaimer, the term of this patent is extended or adjusted under 35 U.S.C. 154(b) by 957 days.

(21) Appl. No.: 11/964,728

(22) Filed: Dec. 27, 2007

(65) Prior Publication Data
US 2008/0161813 A1 Jul. 3, 2008

Related U.S. Application Data

(60) Provisional application No. 60/882,923, filed on Dec. 30, 2006.

(51) Int. Cl.
*A61B 17/00* (2006.01)
(52) U.S. Cl. .............................. 606/81; 606/79; 606/91
(58) Field of Classification Search .............. 606/79–81, 606/83, 84; 407/64, 33, 34, 54; 409/143; 241/91–93
See application file for complete search history.

(56) References Cited

U.S. PATENT DOCUMENTS

| 2,342,892 | A | * | 2/1944 | Prinz | 241/91 |
| 4,802,468 | A | * | 2/1989 | Powlan | 606/81 |
| 5,499,984 | A | * | 3/1996 | Steiner et al. | 606/80 |
| 6,106,536 | A | * | 8/2000 | Lechot | 606/180 |
| 2004/0133209 | A1 | * | 7/2004 | Chappuis | 606/80 |

FOREIGN PATENT DOCUMENTS

| DE | 8709738.9 | | 9/1987 |
| DE | 18532898 | A1 | 3/1997 |
| WO | 03/030748 | A1 | 4/2003 |
| WO | 03/086208 | A1 | 10/2003 |
| WO | 03/092513 | A1 | 11/2003 |

OTHER PUBLICATIONS

International Search Report, PCT/IB2007/004126, dated Aug. 7, 2008.
Vendittoli, P.A., A Randomised Study Comparing Resection of Acetabular, Bone at Resurfacing and Total Hip Replacement, The Journal of Bone & Joint Surgery (Br). vol. 88-B, No. 8, Aug. 2006, Montreal. Canada.

* cited by examiner

*Primary Examiner* — Thomas C. Barrett
*Assistant Examiner* — Andrew Yang
(74) *Attorney, Agent, or Firm* — Michael F. Scalise (57) ABSTRACT

An acetabular reamer (10, 10', 10") is intended in particular for the shaping of the cotyloid cavity in the event of a replacement of a hip joint by total prosthesis. The reamer (10, 10', 10") is typically of a truncated hemispherical form and is adapted for attachment to a reamer spindle in order to be driven in rotation about a cutter axis (11). The ability to cut a full, continuous hemisphere to the apex (12) of the hemispherical body (14) is suppressed, so as to attain the principal advantage of the invention, namely, to adequately prepare the acetabulum for receipt of a prosthesis while minimizing the possibility of breakthrough of the fovea/acetabular fossa. The reamer (10, 10', 10") has an interface 16 typically made tip of cross bars (20) which a holder engages for rotationally activating the reamer for cutting.

20 Claims, 15 Drawing Sheets

CUT-OFF ACETABULAR REAMER

CROSS REFERENCE TO RELATED APPLICATIONS

The present application claims priority to prior filed U.S. Provisional Application Ser. No. 60/882,923 filed 30 Dec. 2006, which is incorporated herein by reference thereto.

BACKGROUND OF THE INVENTION

The invention relates to surgical products, and in particular, to surgical reamers for cutting shaped cavities in bone.

In order to produce a shaped cavity in bone for a hip implant, which requires smooth walls and accurate shape, it is advantageous that the reamer shell or cutting bowl be hemispherical. Further, the cutting teeth must be properly located and oriented.

It is increasingly important, especially with cementless hip surgery, that the acetabulum be reamed to an exact form, generally a hemisphere, thus allowing optimal contact between the bone and the definitive (usually hemispherical) implant.

Further, there is increasing emphasis on cutting a smaller incision to minimize the trauma to the patient and to improve the rate of recovery. Meeting this additional requirement provides an additional challenge to the designers of medical instruments and implants. In addition, the change in surgical procedure includes the fact that the surgeon now more often maintains the acetabular reamer handle on a single axis rather than performing the step of "sweeping" the end of the tool handle through an angle and thus continuously changing the axis of the reamer cut. When a prior art reamer handle is powered, pressed against the acetabulum and maintained on a constant axis such as that described in U.S. Pat. No. 6,001,105, to Salyer, filed Jan. 19, 1998, a series of concentric rings are cut that, on a macro-scale, approximate a hemisphere. When the surgeon "sweeps" the axis of the reamer handle, these irregularities are removed (in a similar manner to polishing) yielding a hemispherical surface. In an attempt to overcome this problem, U.S. Pat. No. 5,116,165 to Sayler, the content of which is incorporated herein by reference, describes a reamer having a limited number of discrete blade-like teeth, which therefore cuts a spline more approximating a perfect hemisphere. Despite the mention of these references as "prior art", nothing herein should be construed as an admission that the present invention is not entitled to antedate such material by virtue of prior invention.

The inventor(s) of the instant application have also invented a reamer that does not requiring a sweeping operation, such reamer being described in U.S. patent application Ser. No. 10/500,944, entitled "Contour Reamer Teeth", filed Jan. 16, 2003, the content of which is incorporated herein by reference thereto.

Re-surfacing of the hip has become popular. There is accumulating evidence that minimal Resection of the femoral head is an effective alternative procedure. Surgeons now consider that the same principle should be applied to the acetabulum and the bone should only be minimally resected prior to cup placement (such as described in an article entitled «A randomized study comparing resection of the Ace tabular bone at resurfacing and total hip replacement. «P. A. Vendittoli et al. JBJS Br 2006 88-B: 997-1002, the content of which are incorporated herein by reference).

Minimal resection is particularly applicable to the acetabulum as it has a paper-thin translucent floor which can sometimes be damaged when using a conventional hemispherical reamer, given that sweeping using a conventional reamer cannot be avoided, and so the full hemispherical shape of the sweep can sometimes break through this thin floor.

Study of the anatomy of the acetabulum shows that articulation occurs only on the C-shaped articular surface and not on the fovea/acetabular fossa (the floor). In other words, there is no need to cut, resurface or resect the apex area of the acetabulum, and consequently, it should be avoided.

Therefore, what is needed is a reamer that reams on the outer areas of the acetabulum and not the paper-thin translucent floor.

SUMMARY OF THE INVENTION

An acetabular reamer is intended in particular for the shaping of the cotyloid cavity in the event of a replacement of a hip joint by total prosthesis. The reamer is typically of a truncated hemispherical form and is adapted for attachment to a reamer spindle in order to be driven in rotation about a cutter axis. Consequently, it is no longer necessary to cut a full, continuous hemisphere up to the apex of the hemispherical body, thereby attaining the principal advantage of the invention, namely, to adequately prepare the acetabulum for receipt of a prosthesis while minimizing the possibility of breakthrough of the fovea/acetabular fossa. The reamer has an interface typically made up of cross bars which a holder engages for rotationally activating the reamer for cutting.

An object of the invention is to preserve bone via minimal resection of the acetabulum—in this manner, the floor of the acetabulum is not destroyed so avoiding break-through and destruction of the medial wall during reaming.

A further object is to optimize a surgeon's visibility during the reaming process.

DETAILED DESCRIPTION OF THE PREFERRED EMBODIMENT

Figure 1A:
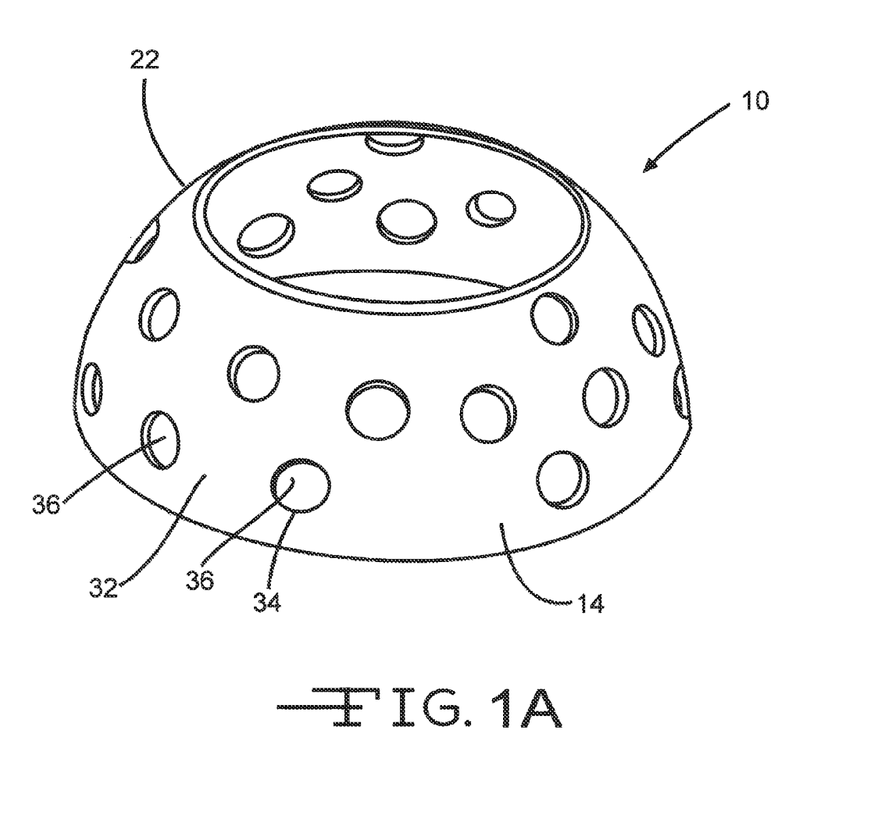
FIG. 1A is a perspective view of a reamer of the invention.
Figure 1B:
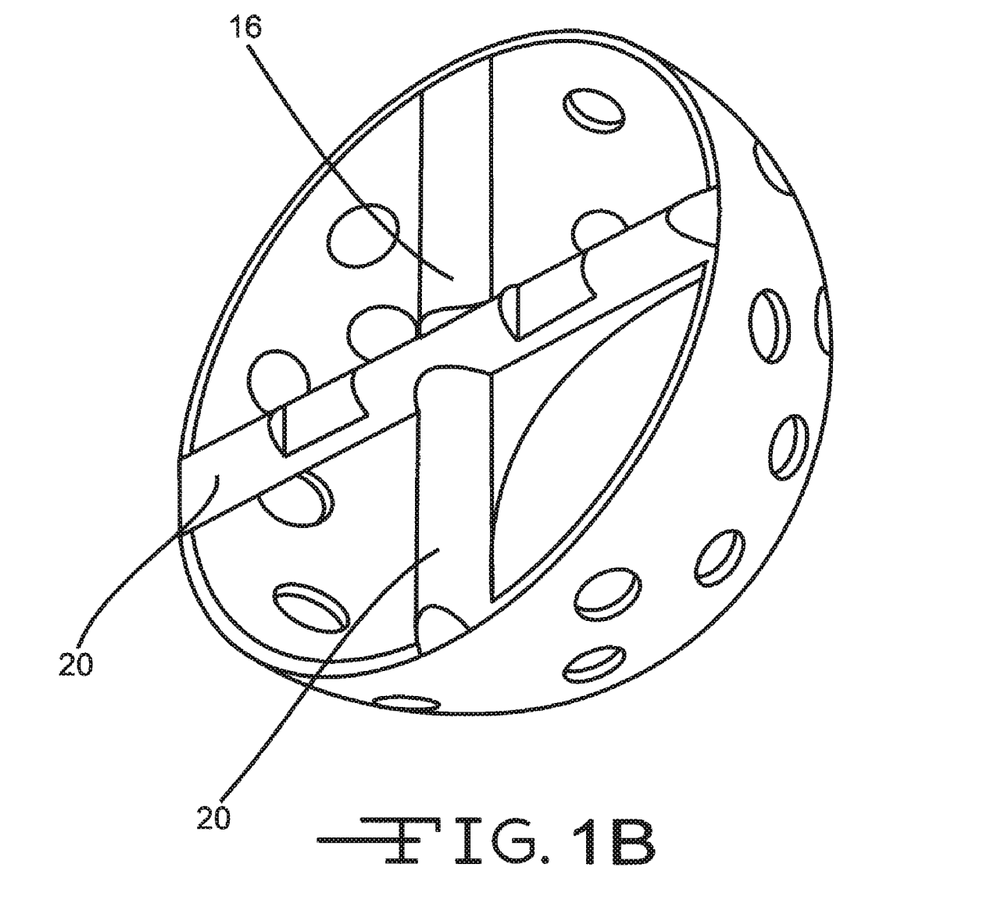
FIG. 1B is a second perspective view of the reamer of the invention.
Figure 1C:
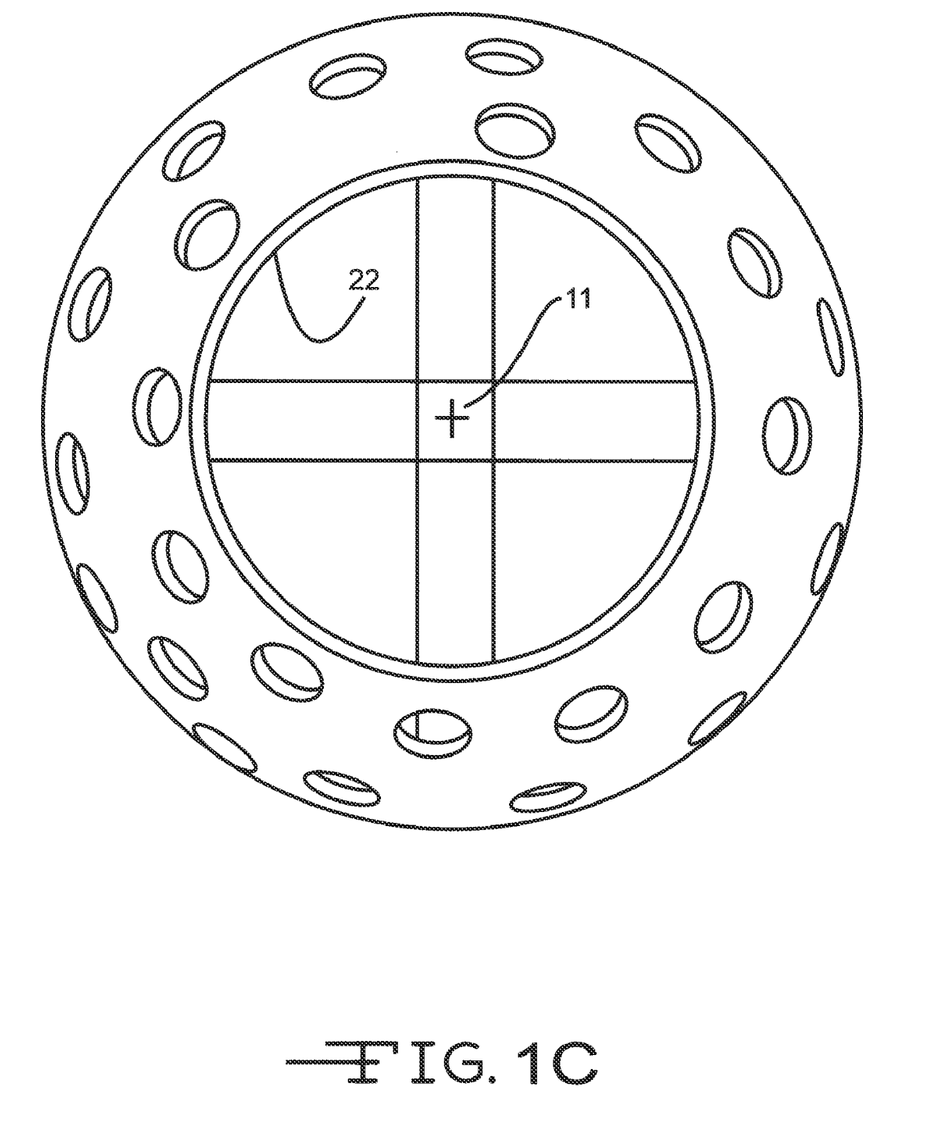
FIG. 1C is a top view of the reamer of the invention.
Figure 1D:
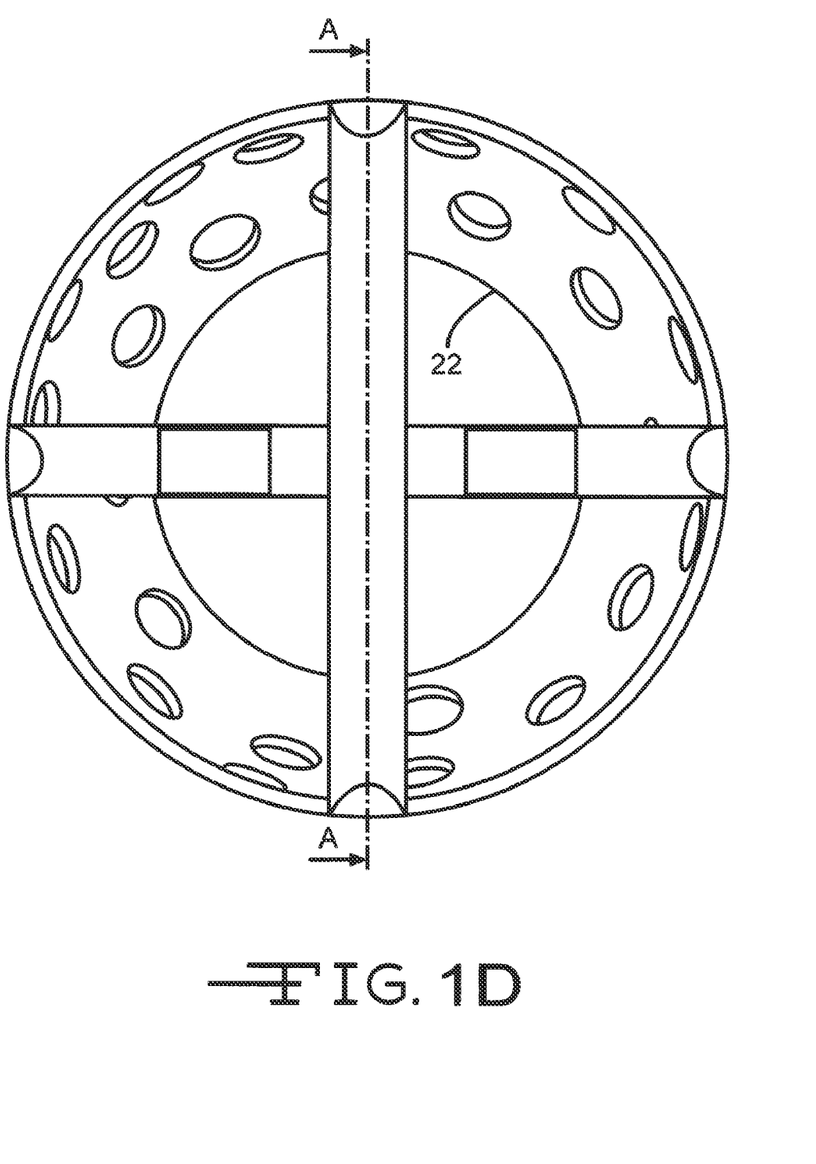
FIG. 1D is a bottom view of the reamer of the invention.

Referring now to FIG. 1A, the reamer 10 of the invention is an acetabular reamer intended in particular for the shaping of the cotyloid cavity in the event of a replacement of a hip joint by total prosthesis. The reamer 10 is typically of a truncated hemispherical form and is adapted for attachment to a reamer spindle in order to be driven in rotation about a cutter axis 11. The necessity to cut a full, continuous hemisphere to the apex 12 of the hemispherical body 14 is suppressed, so as to attain the principal advantage of the invention, namely, to adequately prepare the acetabulum for receipt of prosthesis while minimizing the possibility of breakthrough of the fovea/acetabular fossa (the paper-thin translucent floor of the acetabulum). The reamer 10 has an interface 16 typically comprising cross bars 20, which a holder (not shown) engages for rotationally activating the reamer for cutting. A reamer of the prior art is described in U.S. patent application Ser. No. 10/208,856, entitled Surgical Reamer, the content of which is incorporated herein by reference thereto.

Preferably, the edge 22 is smoothed or formed so as to curve inwardly away from the hemispherical form of the body 14, in order to minimize the chance of cutting the acetabulum at this edge and to reinforce the structure of the reamer 10 so as to prevent buckling or other deformation while supporting the associated cutting forces.

Figure 2A:
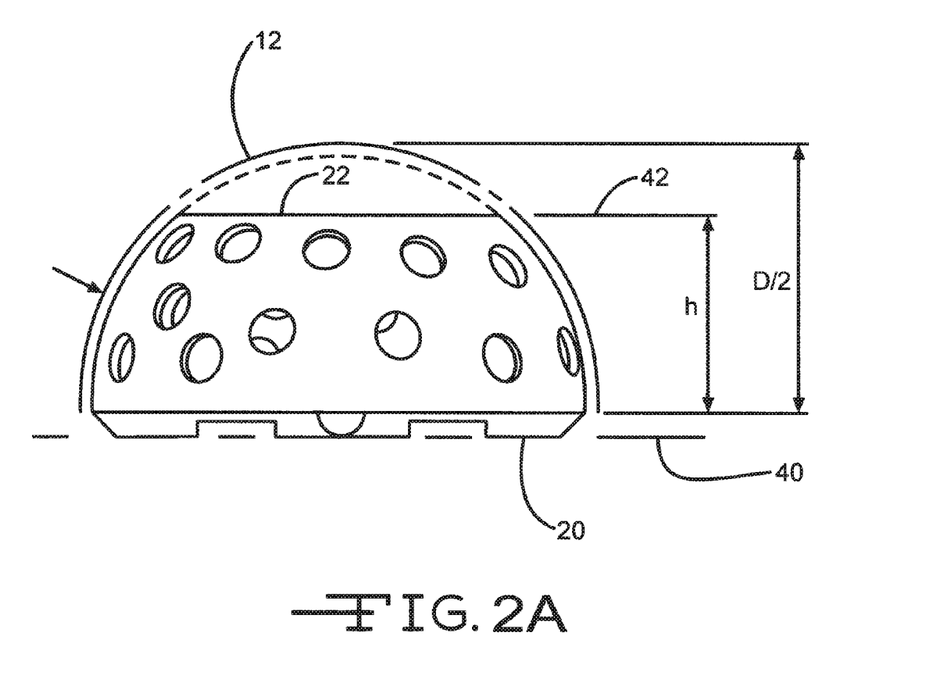
FIG. 2A is a side view of the reamer of the invention.
Figure 2B:
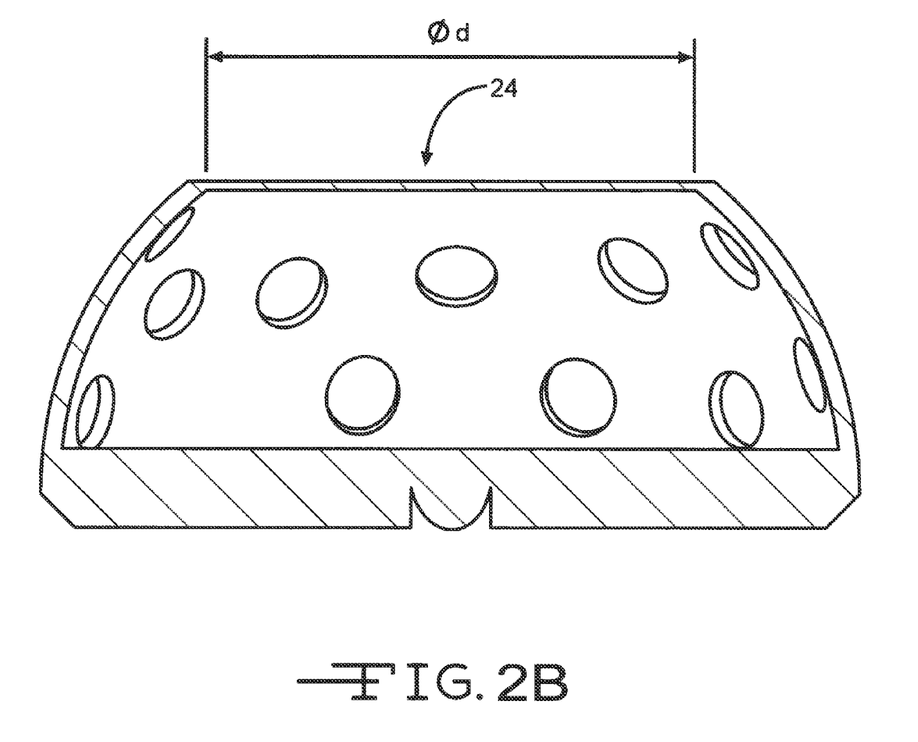
FIG. 2B is a side cross-sectional view of the reamer of the invention.

Referring now to FIGS. 2A and 2B, the reamer 10 has a height h that is less than half of the diameter D of the hemispherical body 14. The truncated opening 24 can be covered with a plate or annular disc (e.g., item 25 and 26 of FIG. 5 and item 26' in FIG. 6), or a cap 30 (as shown in FIGS. 3A-4), although it may also be left largely open as shown.

The body 14 further has an external surface 32 presenting multiple cutting teeth 34 with associated perforations 36 for removal of tissue particles during the cutting operation. The reamer body 14 is formed of a sector of a hemisphere, the sector having first and second planar sides 40 and 42, respectively. The first and second planar sides 40 and 42 are oriented in parallel planes.

Figure 3A:
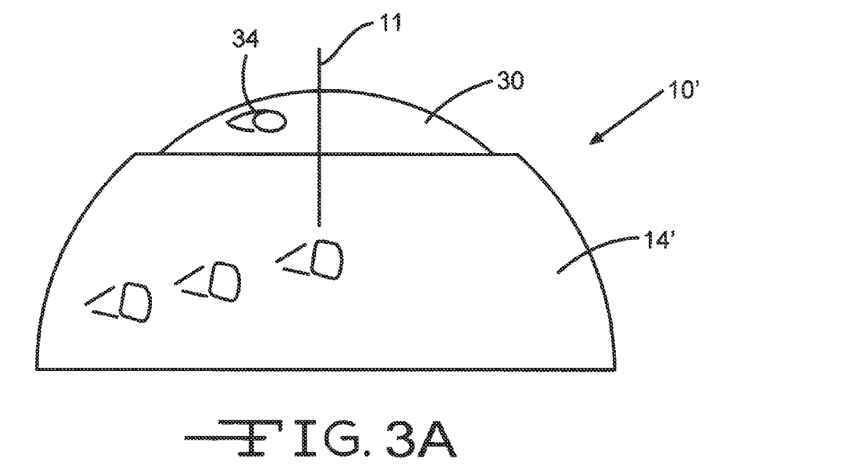
FIG. 3A is a side view of a second embodiment of the reamer of the invention.
Figure 3B:
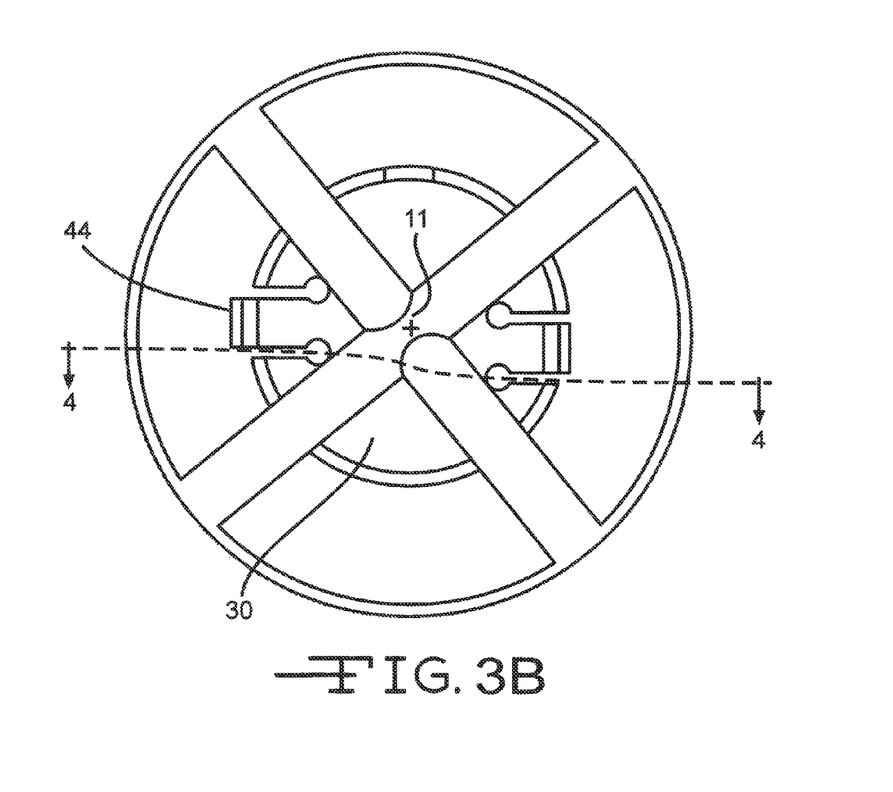
FIG. 3B is a bottom view of the second embodiment of the reamer of the invention.
Figure 4:
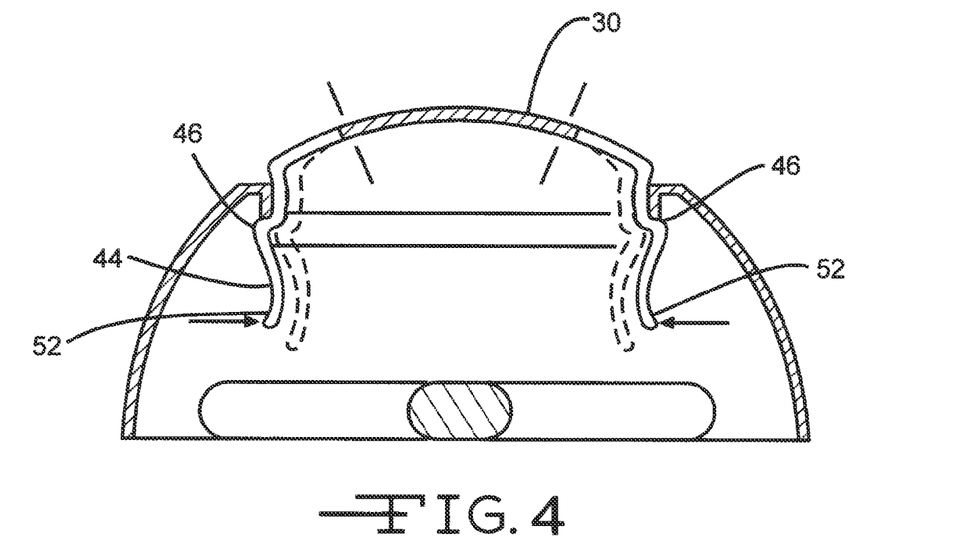
FIG. 4 is a side cross-sectional view of the second embodiment of the reamer of the invention.
Figure 5:
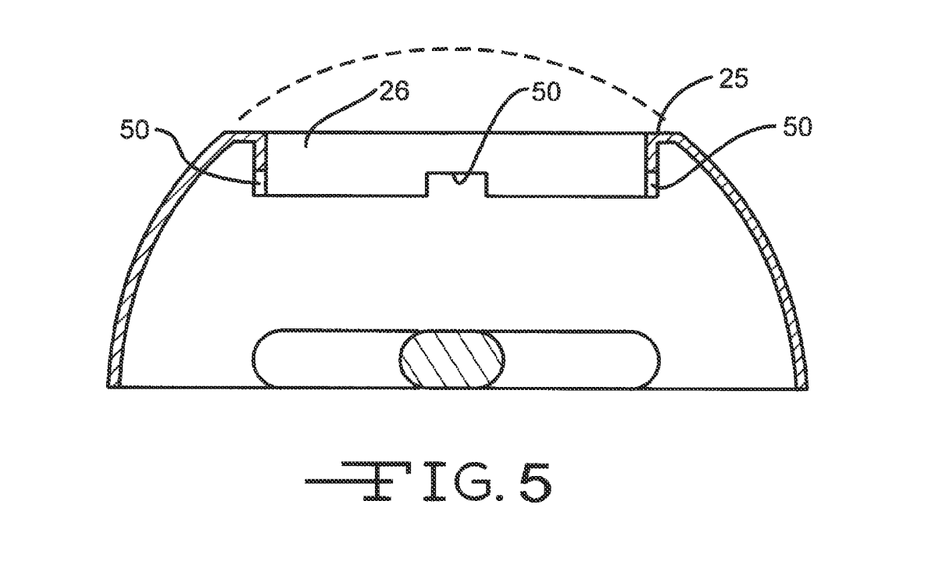
FIG. 5 is a side cross-sectional view of the second embodiment of the reamer of the invention, minus a removable cap.

Referring now to FIGS. 3A, 3B, and 4, in an alternate embodiment, the cap 30 covers the opening 24 of the reamer body 14' and engages with the body so as to rotate with the body when cutting. In this manner, any teeth 34 on the cap 30 cut with the teeth on the body 14. These teeth 34, however, are recessed way from the surface of a perfect hemispherical form including the cutting walls, in order to avoid or minimize the cutting of the floor of the acetabulum.

In an embodiment, the cap 30 has tangs 44 having a pawl form 46 extending therefrom into keyways 50 (best shown in FIG. 4) in the annular flange 26 of the body 14. The tangs 44 further have extending finger engagement ears 52 to permit a surgeon's fingers to engage and urge opposing tangs toward one another in order to remove or install the cap 30 into the opening 24 of the reamer 10'.

Figure 6:
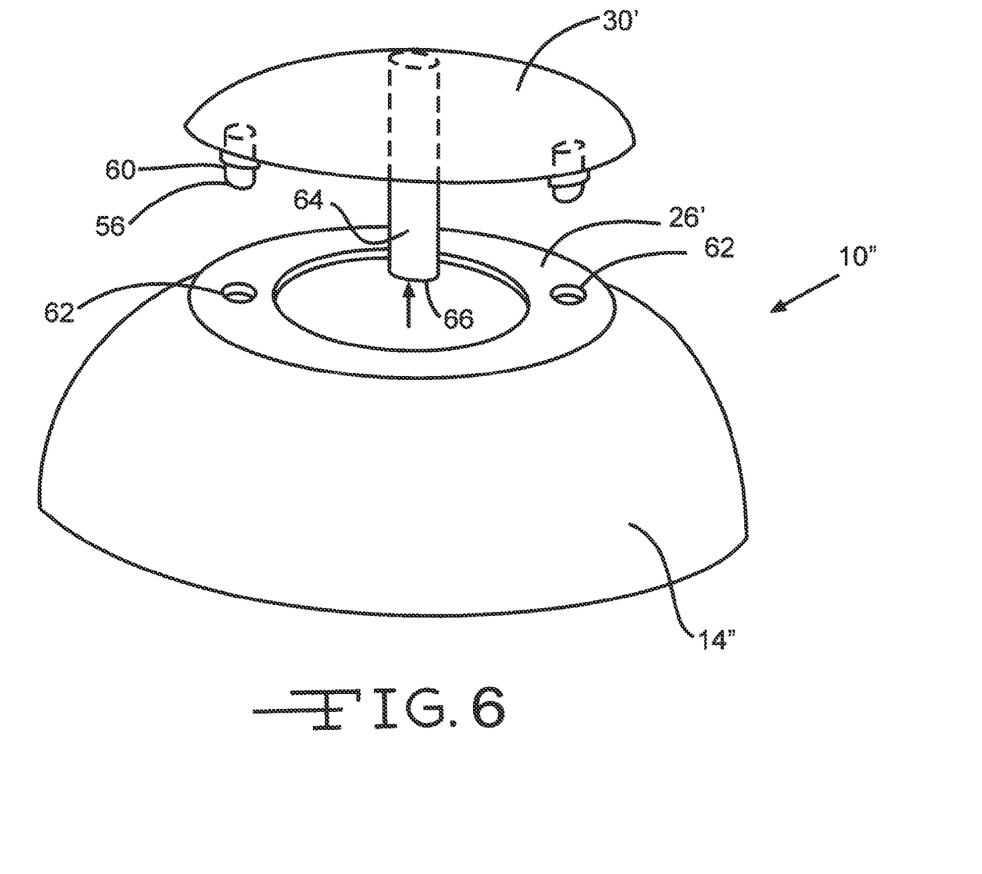
FIG. 6 is a perspective, exploded view of a third, simplified embodiment of the reamer of the invention.

Referring now to FIG. 6, in an alternative, simplified embodiment, the body 14" engages with a cap 30'. The cap 30' has a stud or studs 56, each having a retainer clip or ring, 60 (improve drawing showing retainer clip) engaged in a recess therein. The studs 56 engage in holes 62 in the disc 26' of the body 14" such that the cap 30' rotates with reamer 10" when cutting. In order to facilitate removal, a stem 64 extends from the apex of cap 30', thereby providing a surface 66 against which a user can press to remove the cap when not needed.

Considering the anatomy of the acetabulum, articulation, i.e., bone-to-socket contact, occurs only on the outer-most regions of the acetabulum articular surface and not on the fovea/acetabular fossa (the floor). Therefore, a cup prosthesis need not be fully hemispherical to be effective. Further, reaming using the invention, i.e., cut-off acetabular reamer, a cut-off hemispherical shape will preserve more of the floor of the acetabulum. Consequently, the invention is a reamer that reams the outermost regions of the cotyloid cavity area of the acetabulum and not the paper-thin translucent floor (arrow). The end result will be a hemispherically reamed acetabulum with an intact medial wall.

Figure 7A:
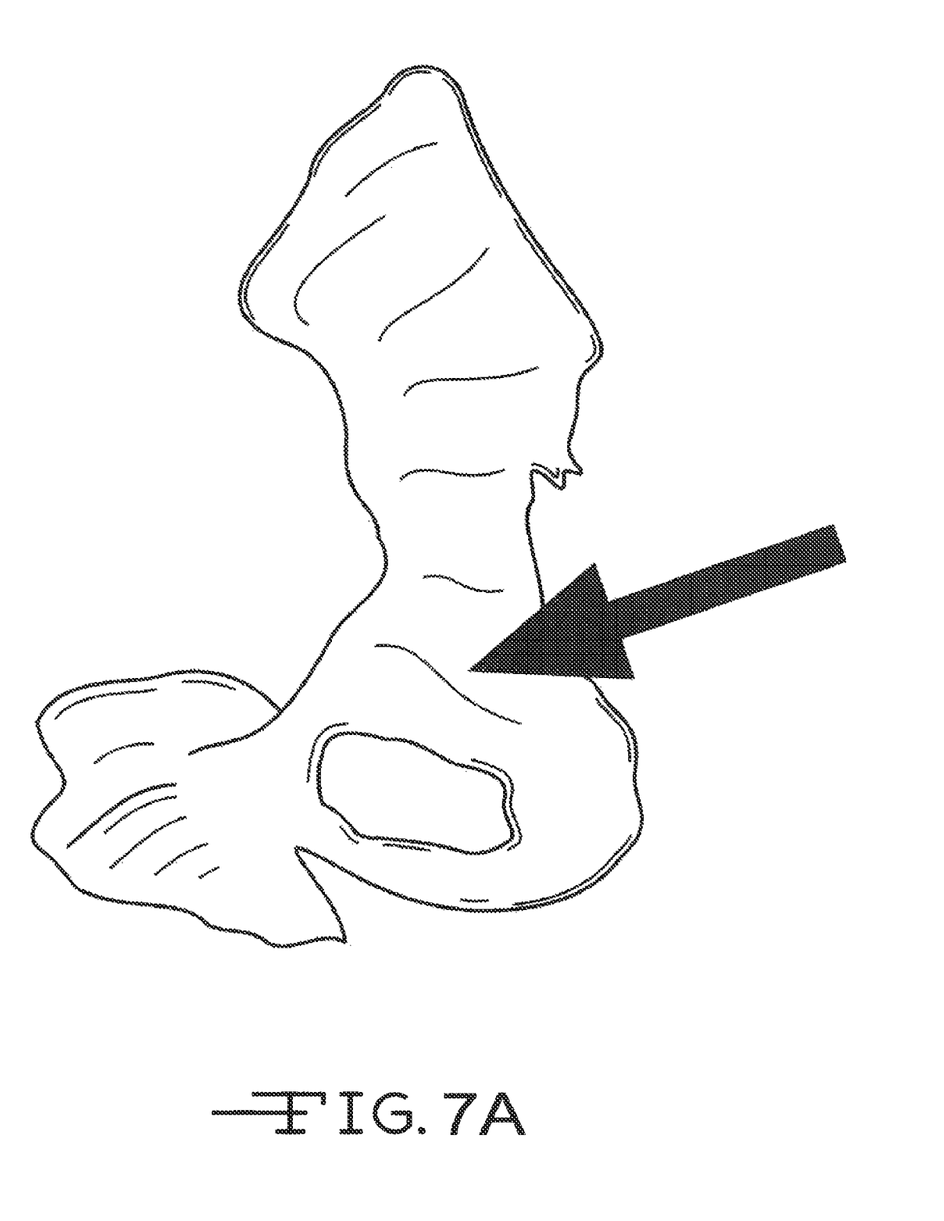
FIG. 7A shows the floor of the acetabulum.

Referring now to FIG. 7A the acetabulum including the floor thereof (see arrow) is shown. The floor or fossa, is paper thin and translucent. It is important to ensure that after reaming, the floor of the acetabulum is not destroyed so avoiding break-through and destruction of the medial wall.

Figure 7B:
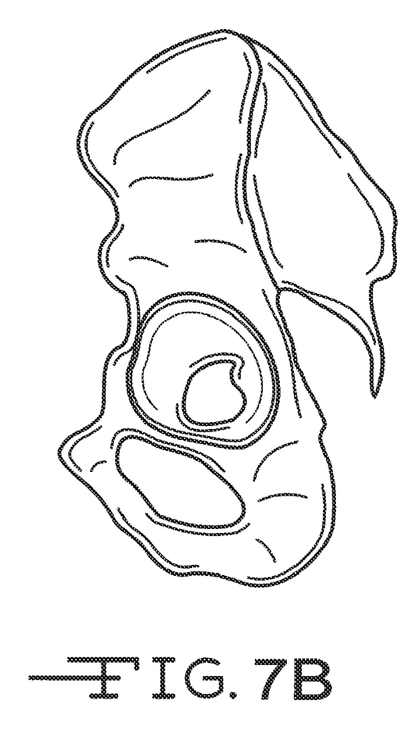
FIGS. 7B-7C shows an acetabulum damaged using a reamer of the prior art.
Figure 7C:
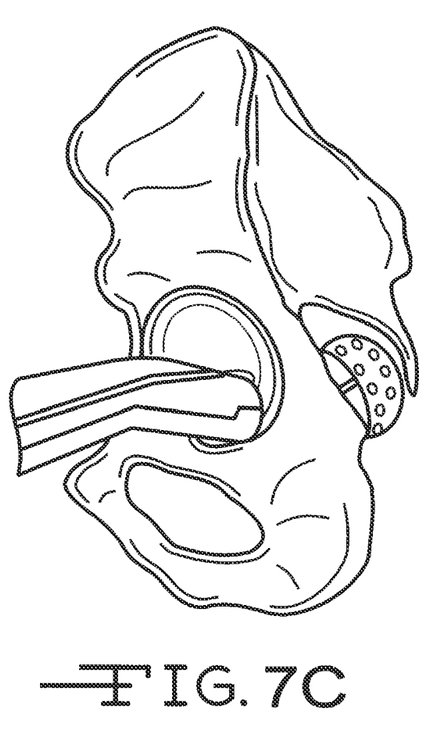

FIGS. 7B and 7C show the acetabulum damaged by reaming using the reamer of the prior art, where the fossa was too thin to avoid breakthrough.

Referring now to FIGS. 5A to 8G, the method of reaming using the reamer 10, 10', 10" of the invention involves several steps. In a first step, the size of the reamer 10, 10', and 10" of the reamer is selected, using data from X-rays or from examination of the acetabulum during the operative procedure. In a second step, the reamer 10, 10', 10" attached to the reamer driver, is placed in its position for reaming the acetabulum. As shown in FIG. 8C, the removal of the apex 12 provides the surgeon with excellent visibility of the sensitive thin floor of the acetabulum. The cap 30, 30' may alternatively be made of a transparent plastic, so as to provide the surgeon with visibility of the cotyloid cavity floor.

Figures 8A, 8B, 8C:
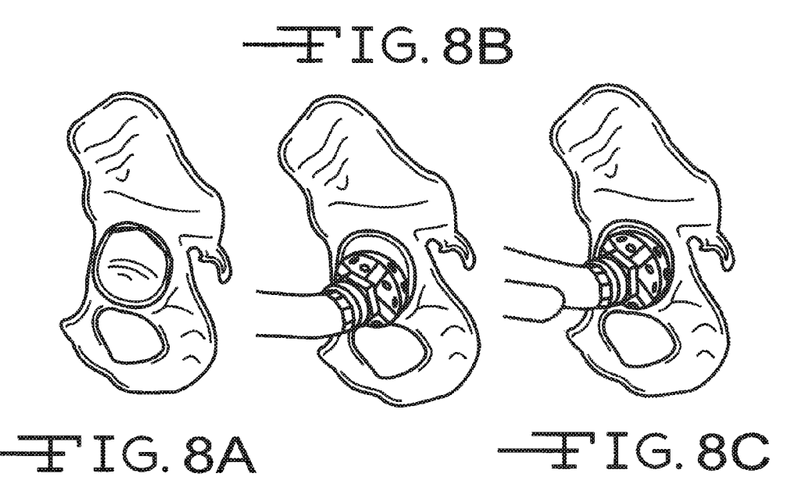
FIGS. 8A-8F are a pictorial progression of the steps of the method of the invention.
Figures 8D, 8E, 8F:
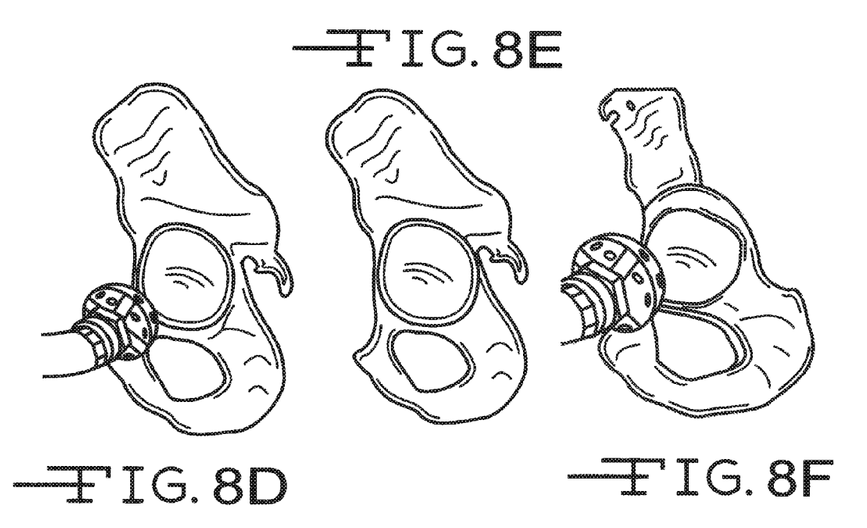

Referring now to FIG. 8D, a partially reamed acetabulum is shown. Progressively more reaming is shown in FIG. 8E. FIG. 8F shows the acetabulum, fully reamed, with the floor thereof untouched.

Figure 9:
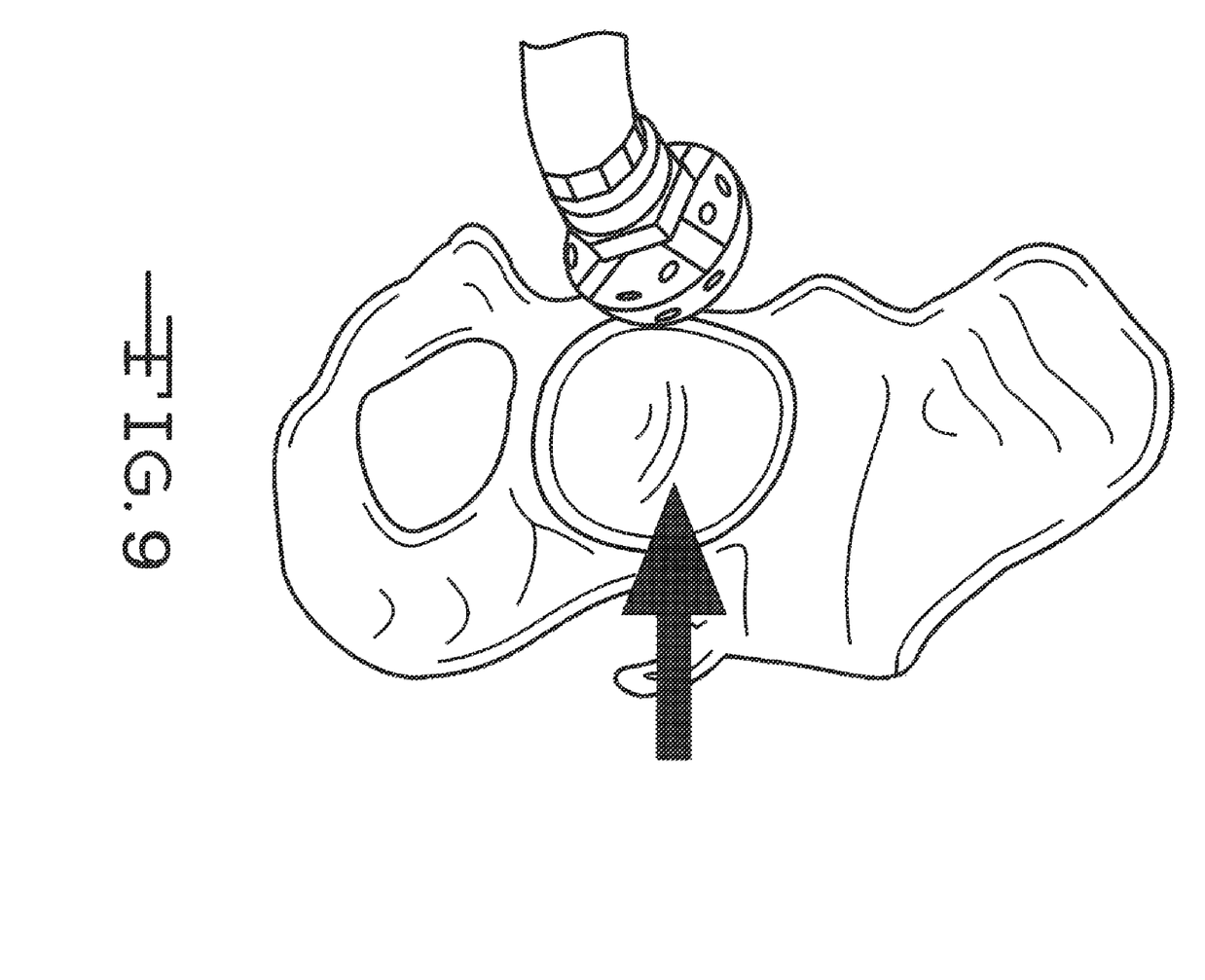
FIG. 9 is a pictorial representation of the floor of the acetabulum, still intact after reaming with the reamer of the invention.

Even with still further reaming, shown in FIG. 9, the floor remains fully intact (see arrow).

The concept of this reamer is that the acetabulum often has the form of a flattened C-shape (flattened on the left side of the "C"), flattened in the region of the fossa, or simply has a very thin apexial wall, articulating and supporting load at the outer areas where the articular cartilage is. Consequently, only this load-bearing area needs to be reamed. The medial wall is very thin and very often surgeons inadvertently ream a large hole in the floor of the acetabulum which may then require the additional step of bone grafting. This is something essentially every surgeon is concerned about and wishes to avoid.

It is believed that an optimal size of the hole at the top of the cut-off reamer 10, 10', 10" of the invention has a radius of 1.5 cm for a size 54 acetabulum. This ratio 1.5/54 may be used to scale for reamers of different sizes (for example, size 40 to >60).

Further, it is believed that a reamer 10, 10', 10" which is made of a spherical form which consists of a hemisphere in which the apex 12 is recessed and located at a distance of about ⅔ of the radius of the hemisphere, as measured from the equator, operates as a cut-off reamer, in particular, where this reamer has teeth located only in the lower ⅔ of hemispherical shape of the reamer.

Figure 10:
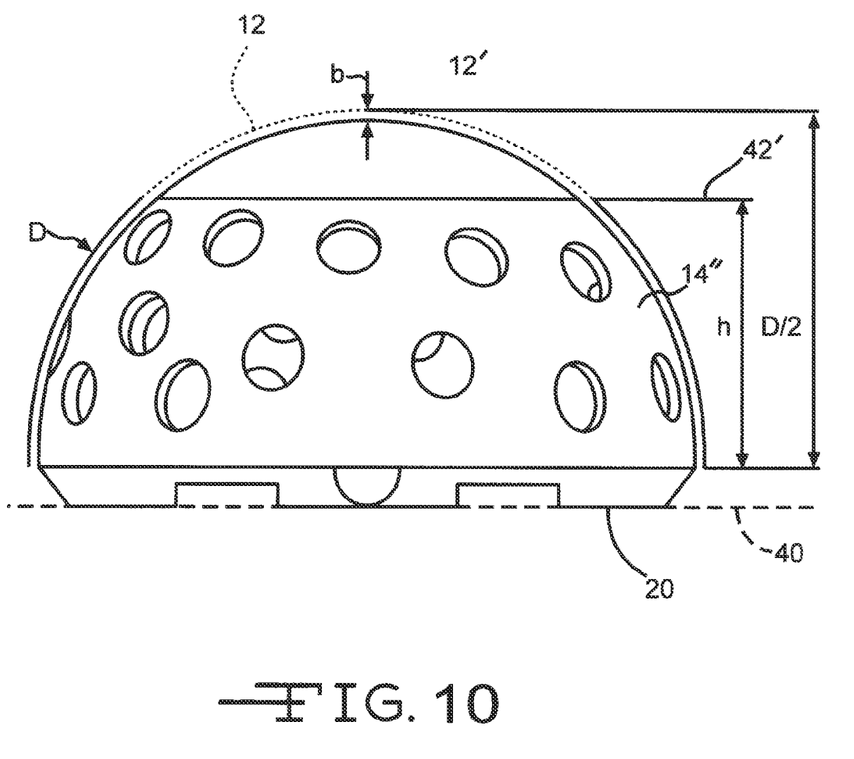
FIG. 10 is an alternate embodiment of the invention.

Referring now to FIG. 10, in another embodiment, a substantially hemispherical reamer similar to the prior art is used, but with significant differences in that the teeth 34 are only disposed on the lower ⅔ portion 14" of the hemisphere, and the apex portion is not removed, but rather remains smooth. However, as already mentioned, it is envisioned that some recessing or insetting of the hemispherical apex portion 12' is required to account for the amount of bone to be cut (dimension b) by the lower ⅔ portion, so as not to tend to apply increasing pressure on the floor as the cutting portion cuts the sides and to provide a stop against further cutting of the acetabulum.

Figure 11:
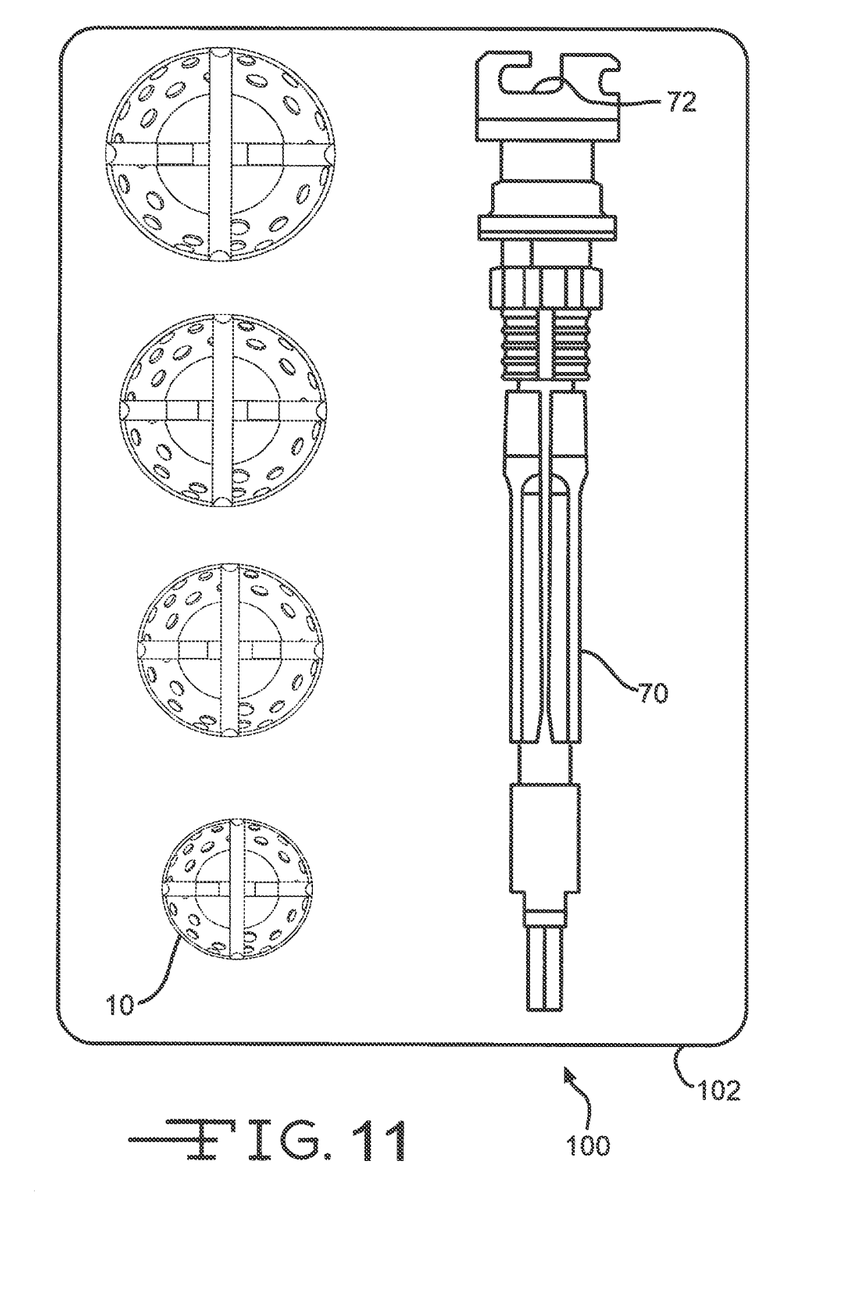
FIG. 11 is a plan view of a kit of the invention.

Referring now to FIG. It, a kit 100 of the invention includes an assortment of reamers 10, 10', 10" of various sizes, a reamer spindle 70, all arranged in a case 102 that conveniently ordered kit components to be readily identifiable and available during a surgical procedure.

In an advantage, the system and method of the invention preserves bone with minimal resection of the acetabulum—the floor of the acetabulum is not destroyed so avoiding breakthrough and destruction of the medial wall during reaming.

In a further advantage, a surgeon's visibility is more optimized during the reaming process.

In a still further advantage, reaming is made more efficient because less torque inputs are required to cut the acetabulum (i.e., unnecessary cutting, which would otherwise consume energy and effort, is avoided).

Multiple variations and modifications are possible in the embodiments of the invention described here. Although certain illustrative embodiments of the invention have been shown and described here, a wide range of modifications, changes, and substitutions is contemplated in the foregoing disclosure. While the above description contains many specifics, these should not be construed as limitations on the scope of the invention, but rather as exemplifications of one or another preferred embodiment thereof. In some instances, some features of the present invention may be employed without a corresponding use of the other features. For example, an implant in a hip socket is best fixed to a concave, hemispherical cavity. However, such a shape is not strictly necessary. Other acetabular cutting shells are non-hemispherical and so the principle explained here may be adapted to include such other geometries. Accordingly, it is appropriate that the foregoing description be construed broadly and understood as being given by way of illustration and example only, the spirit and scope of the invention being limited only by the appended claims.

What is claimed is:

1. A reamer suitable for cutting bone, the reamer comprising:
   a) an interface for connection to a reamer spindle in order to be driven in rotation about a cutter axis; and
   b) a reamer body connected to the interface, the reamer body having multiple cutting sites and comprising a dome portion of a hemisphere extending from a lower edge defining a lower perimeter to an intermediate edge defining an intermediate perimeter located on an imaginary intermediate plane that is spaced from and positioned between an imaginary apex of the dome portion and the lower edge, wherein the lower perimeter of the lower edge is greater than the intermediate perimeter of the intermediate edge, and
   c) wherein the interface is at least one reinforcement bar connected to spaced apart locations of the dome portion, and
   d) wherein the dome portion is rotatable about the cutter axis, which passes through the imaginary apex and is perpendicular to an imaginary equatorial plane of the hemisphere.

2. The reamer of claim 1 wherein the at least one reinforcement bar is adapted to interface with bayonet catches in a reamer spindle.

3. The reamer of claim 1 wherein the interface comprises intersecting bars which connect to spaced apart locations of the dome portion.

4. The reamer of claim 3 wherein the intersecting bars are connected to spaced apart locations on the lower edge of the dome portion.

5. The reamer of claim 3 wherein the intersecting bars are adapted to be received in one or more bayonet catches of a reamer spindle.

6. The reamer of claim 1 wherein the reamer is adapted for cutting a cotyloid cavity of an acetabulum.

7. The reamer of claim 1 wherein the intermediate edge spaced from the imaginary apex forms an aperture in the reamer body.

8. The reamer of claim 7 wherein the aperture is coverable with a removable cap.

9. The reamer body of claim 8 wherein the removable cap is made of a transparent material.

10. The reamer of claim 1 wherein the intermediate edge spaced from the imaginary apex is a non-toothed portion of the reamer body.

11. The reamer of claim 1 wherein the cutting sites comprise apertures suitable for passing debris into a cavity defined by an inner surface of the dome portion where the debris may accumulate.

12. The reamer of claim 1 wherein each cutting site is immediately adjacent to a perforation in the reamer body for removal of tissue particles.

13. A tool kit for surgical use, the kit including:
   a) an assortment of reamers according to claim 1 of various sizes,
   b) a reamer spindle, and
   c) a case containing the reamers and the reamer spindle.

14. The reamer of claim 1 wherein the intermediate edge is an annular edge defining the intermediate perimeter.

15. The reamer of claim 1 wherein the lower edge of the dome portion resides on the imaginary equatorial plane of the hemisphere.

16. The reamer of claim 15 wherein the imaginary equatorial plane defined by the lower edge and the imaginary intermediate plane of the intermediate edge are parallel to each other.

17. A reamer rotatable about a cutting axis for cutting bone, the reamer comprising:
   a) an interface for connection to a reamer spindle in order to be driven in rotation about a cutter axis; and
   b) a reamer body connected to the interface, the reamer body having multiple cutting teeth thereon and comprising a dome portion of a hemisphere extending from a lower edge defining a lower perimeter residing on an imaginary equatorial plane to an intermediate annular edge defining an intermediate perimeter located on an imaginary intermediate plane that is spaced from and positioned between an imaginary apex of the dome portion and the lower edge, wherein the lower perimeter of the lower edge is greater than the intermediate perimeter of the intermediate edge, and
   c) wherein the interface is at least one reinforcement bar connected to spaced apart locations of the dome portion, and
   d) wherein the dome portion is rotatable about the cutter axis, which passes through the imaginary apex and is perpendicular to the imaginary equatorial plane.

18. The reamer of claim 17 wherein the imaginary equatorial plane defined by the lower edge and the imaginary intermediate plane of the intermediate annular edge are parallel to each other.

19. The reamer of claim 17 wherein the at least one reinforcement bar is connected to spaced apart locations on the lower edge of the dome portion.

20. A reamer suitable for cutting bone, the reamer comprising:
   a) an interface for connection to a reamer spindle in order to be driven in rotation about a cutter axis; and
   b) a reamer body connected to the interface, the reamer body being substantially in the form of a portion of a hemisphere having a recess about an imaginary apex of the hemisphere so as to cut less than a full hemisphere about the apex, c) wherein the reamer body has cutting teeth thereon formed exclusively in a region about an imaginary equator of the reamer body upward to a plane parallel with the apex and recessed from the apex toward the imaginary equator by a distance approximately equal to one third of the radius of the reamer body.

* * * * *